United States Patent
Vaez-Iravani et al.

(10) Patent No.: US 6,922,236 B2
(45) Date of Patent: Jul. 26, 2005

(54) SYSTEMS AND METHODS FOR SIMULTANEOUS OR SEQUENTIAL MULTI-PERSPECTIVE SPECIMEN DEFECT INSPECTION

(75) Inventors: Mehdi Vaez-Iravani, Los Gatos, CA (US); Stan Stokowski, Danville, CA (US); Steven Biellak, Sunnyvale, CA (US); Jamie Sullivan, Sunnyvale, CA (US); Keith Wells, Santa Cruz, CA (US); Mehrdad Nikoonahad, Menlo Park, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 391 days.

(21) Appl. No.: 10/192,813

(22) Filed: Jul. 10, 2002

(65) Prior Publication Data

US 2003/0011760 A1 Jan. 16, 2003

Related U.S. Application Data

(60) Provisional application No. 60/304,480, filed on Jul. 10, 2001.

(51) Int. Cl.[7] ............................................. G01N 21/88
(52) U.S. Cl. .................................................... 356/237.2
(58) Field of Search .......................... 356/237.2–237.5, 356/431

(56) References Cited

U.S. PATENT DOCUMENTS

| | | | |
|---|---|---|---|
| 4,110,047 A | * | 8/1978 | Takahashi ................ 356/237.1 |
| 4,391,524 A | | 7/1983 | Steigmeier et al. |
| 4,441,124 A | | 4/1984 | Heebner et al. |
| 4,614,427 A | | 9/1986 | Koizumi et al. |
| 4,650,333 A | * | 3/1987 | Crabb et al. .............. 356/237.5 |
| 4,889,998 A | * | 12/1989 | Hayano et al. .......... 356/239.8 |
| 5,017,798 A | * | 5/1991 | Murakami et al. .......... 356/431 |
| 5,096,291 A | | 3/1992 | Scott |
| 5,317,380 A | | 5/1994 | Allemand |
| 5,565,979 A | * | 10/1996 | Gross ...................... 356/237.2 |
| 5,883,710 A | | 3/1999 | Nikoonahad et al. |
| 5,917,588 A | | 6/1999 | Addiego |
| 6,020,957 A | | 2/2000 | Rosengaus et al. |
| 6,201,601 B1 | * | 3/2001 | Vaez-Iravani et al. ... 356/237.4 |
| 6,215,551 B1 | | 4/2001 | Nikoonahad et al. |

* cited by examiner

Primary Examiner—Richard A. Rosenberger
(74) Attorney, Agent, or Firm—Ann Marie Mewherter; Daffer McDaniel, LLP

(57) ABSTRACT

Systems and methods for inspecting a surface of a specimen such as a semiconductor wafer are provided. A system may include an illumination system configured to direct a first beam of light to a surface of the specimen at an oblique angle of incidence and to direct a second beam of light to a surface of the specimen at a substantially normal angle. The system may also include a collection system configured to collect at least a portion of the first and second beams of light returned from the surface of the specimen. In addition, the system may include a detection system. The detection system may be configured to process the collected portions of the first and second beams of light. In this manner, a presence of defects on the specimen may be detected from the collected portions of the first and second beams of light.

26 Claims, 8 Drawing Sheets

SYSTEMS AND METHODS FOR SIMULTANEOUS OR SEQUENTIAL MULTI-PERSPECTIVE SPECIMEN DEFECT INSPECTION

PRIORITY CLAIM

This application claims priority to U.S. Provisional Application No. 60/304,480 entitled "Systems and Methods for Simultaneous or Sequential Multi-Perspective Specimen Defect Inspection," filed Jul. 10, 2001.

BACKGROUND OF THE INVENTION

1. Field of the Invention

The present invention generally relates to systems and methods for inspecting a specimen. Certain embodiments relate to systems and methods that include inspecting a specimen with simultaneous or sequential multi-angle illumination.

2. Description of the Relevant Art

Fabricating semiconductor devices such as logic and memory devices may typically include processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes may include, but are not limited to, chemical-mechanical polishing, etch, deposition, and ion implantation. Multiple semiconductor devices may be fabricated in an arrangement on a semiconductor wafer and then separated into individual semiconductor devices.

During each semiconductor device fabrication process, defects such as particulate contamination and pattern defects may be introduced into the semiconductor devices. Such defects may be isolated to a single semiconductor device on a semiconductor wafer containing several hundred semiconductor devices. For example, isolated defects may be caused by random events such as an unexpected increase in particulate contamination in a manufacturing environment or an unexpected increase in contamination in process chemicals that may be used in fabrication of the semiconductor devices. Alternatively, the defects may be repeated in each semiconductor device formed across an entire semiconductor wafer. In an example, repeated defects may be systematically caused by contamination or defects on a reticle. A reticle, or a mask, may be disposed above a semiconductor wafer and may have substantially transparent regions and substantially opaque regions that are arranged in a pattern that may be transferred to a resist on the semiconductor wafer. Therefore, contamination or defects on a reticle may also be reproduced in the pattern transferred to the resist and may undesirably affect the features of each semiconductor device formed across an entire semiconductor wafer in subsequent processing.

Defects on semiconductor wafers may typically be monitored manually by visual inspection, particularly in the lithography process because many defects generated during a lithography process may be visible to the naked eye. Such defects may include macro defects that may be caused by faulty processes during this step. Defects that may be visible to the human eye typically have a lateral dimension greater than or equal to approximately 100 $\mu$m. Defects having a lateral dimension as small as approximately 10 $\mu$m, however, may also be visible on unpatterned regions of a semiconductor wafer. An example of a visual inspection method is illustrated in U.S. Pat. No. 5,096,291 to Scott and is incorporated by reference as if fully set forth herein. Prior to the commercial availability of automated defect inspection systems such as the systems illustrated in U.S. Pat. Nos. 5,917,588 to Addiego and U.S. Pat. No. 6,020,957 to Rosengaus et al., which are incorporated by reference as if fully set forth herein, manual inspection was the most common, and may still be the most dominant, inspection method used by lithography engineers.

Automated inspection systems were developed to decrease the time required to inspect a wafer surface. Such inspection systems may typically include two major components such as an illumination system and a collection-detection system. An illumination system may include a light source such as a laser that may produce a beam of light and an apparatus for focusing and scanning the beam of light. Defects present on the surface may scatter the incident light. A detection system may detect the scattered light and may convert the detected light into electrical signals that may be measured, counted, and displayed on an oscilloscope or other monitor. Examples of such inspection systems are illustrated in U.S. Pat. No. 4,391,524 to Steigmeier et al., U.S. Pat. No. 4,441,124 to Heebner et al., U.S. Pat. No. 4,614,427 to Koizumi et al., U.S. Pat. No. 4,889,998 to Hayano et al., U.S. Pat. No. 5,317,380 to Allemand, U.S. Pat. No. 5,883,710 to Nikoonahad et al., and U.S. Pat. No. 6,215,551 to Nikoonahad et al., all of which are incorporated by reference as if fully set forth herein.

SUMMARY OF THE INVENTION

Inspecting specimens such as wafers may be complicated due to, for example, the variety of defects that may need to be detected and a diverse array of background circuitry against which the detection may be performed. Generally, in light scattering systems, for example, a given illumination/collection strategy may be substantially optimized for one category of defects such as particles but may not be very effective for other defect types such as scratches. In this manner, a light scattering system that includes a plurality of illumination/collection systems, each of which, operated simultaneously or sequentially, may have good sensitivity for different defect types. As such, a dual incidence illumination system may detect a larger range of defects than a single incidence system.

A dual incidence illumination system may include, for example, a normal incidence illumination channel and an oblique illumination channel. Such a system may provide uniform scratch sensitivity, as well as the potential for a versatile bright field, excellent pattern defect inspection, background pattern suppression, and foreign particle detection capability. Inspecting a specimen may involve using only one of the plurality of illumination/collection system depending on, for example, a specific application of the inspection. In addition, illumination may vary from site to site across a surface of a specimen. For such illumination, a spot size of a normal incidence beam may be approximately equal to a spot size of an oblique incidence beam. In addition, scanning of the normal incidence beam and the oblique incidence beam may be synchronized for such illumination. Because the illumination/collection systems may operate simultaneously, however, a throughput of such an inspection system may not be reduced due to using additional illumination/collection systems for inspecting a specimen. In addition, such a light scattering system may provide a capability for fast classification of the defects.

An embodiment of the invention relates to a system configured to inspect a specimen such as a wafer. The system may include an illumination system. The illumination system may be configured to direct a first beam of light to a surface of the specimen at an oblique angle of incidence. The oblique angle of incidence may include an angle of incidence from approximately 5° to approximately 80°. For example, the oblique angle of incidence may be approximately 70°. The illumination system may also be configured to direct a second beam of light to a surface of the specimen at a substantially normal angle. A polarization of the first beam of light may be substantially orthogonal to a polarization of the second beam of light. In addition, an intensity of the second beam of light may be substantially less than an intensity of the first beam of light. Furthermore, substantially an entire area of the first beam of light incident upon the surface of the specimen may overlap substantially an entire area of the second beam of light incident upon the surface of the specimen.

The illumination system may include a light source configured to generate a beam of light. The illumination system may include a light scanning device configured to direct the generated beam of light at various angles. The light scanning device may be, for example, an acousto-optical deflector. In addition, the illumination system may include a beam splitting device configured to split the directed beam of light into the first beam of light and the second beam of light. The illumination system may be further configured to direct the first and second beams of light to the surface of the specimen substantially simultaneously. Alternatively, the illumination system may be configured to direct the first and second beams of light to the surface of the specimen sequentially.

In an embodiment, the illumination system may also include a pair of anamorphic prisms. The pair of anamorphic prisms may be configured to reduce a diameter of the second beam of light in one direction. In this manner, a shape of the second beam of light incident on the surface of the specimen may be substantially the same as a shape of the first beam of light incident on the surface of the specimen. In addition, the illumination system may include a focusing lens in a non-telecentric geometry positioned in a path of the second beam of light. The focusing lens may be configured to increase the telecentricity of the second beam of light. The illumination system may be arranged in a Mach-Zehnder type arrangement.

In an embodiment, the system may also include a collection system. The collection system may be configured to collect at least a portion of the first beam of light returned from the surface of the specimen. In addition, the collection system may be configured to collect at least a portion of the second beam of light returned from the surface of the specimen. The collection system may include a spatial filter configured to reduce unwanted diffraction orders in the first beam of light scattered from the surface of the specimen. The spatial filter may also be configured to reduce unwanted diffraction orders in the second beam of light scattered from the surface of the specimen. The collection system may include at least two collectors. At least the two collectors may include single dark field collectors, double dark field collectors, near normal dark field collectors, bright field collectors, or any combination thereof.

In an embodiment, the system may also include a detection system configured to process the collected portions of the first and second beams of light. In this manner, a presence of defects on the specimen can be detected from the collected portions of the first and second beams of light. Defects that may be detected from the collected portions of the first and second beams of light may include, but may not be limited to, defects above the surface of the specimen, defects below the surface of the specimen, defects with varying orientations, or any combination thereof.

Another embodiment relates to a method for inspecting a specimen such as a wafer. The method may include illuminating a surface of the specimen with a first beam of light at an oblique angle of incidence and with a second beam of light at a substantially normal angle. The oblique angle of incidence may include an angle of incidence from approximately 5° to approximately 80°. For example, the oblique angle of incidence may be approximately 70°. A polarization of the first beam of light may be substantially orthogonal to a polarization of the second beam of light. In addition, an intensity of the second beam of light may be substantially less than an intensity of the first beam of light. Furthermore, substantially an entire area of the first beam of light incident upon the surface of the specimen may overlap substantially an entire area of the second beam of light incident upon the surface of the specimen.

In an embodiment, illuminating the surface of the specimen may include generating a beam of light and directing the generated beam of light at various angles. In addition, illuminating the surface of the specimen may include splitting the directed beam of light into the first beam of light and the second beam of light. Illuminating the surface of the specimen may include illuminating the surface of the specimen with the first beam of light and the second beam of light substantially simultaneously. Alternatively, illuminating the surface of the specimen may include illuminating the surface of the specimen with the first beam of light and the second beam of light sequentially.

In an embodiment, illuminating the surface of the specimen may include reducing a diameter of the second beam of light in one direction such that a shape of the second beam of light incident on the surface of the specimen is substantially the same as a shape of the first beam of light incident on the surface of the specimen. Illuminating the surface of the specimen may include increasing a telecentricity of the second beam of light with a focusing lens in a non-telecentric geometry positioned in a path of the second beam of light. Illuminating the surface of the specimen may include illuminating the surface of the specimen with an illumination system arranged in a Mach-Zehnder type arrangement.

In an embodiment, the method may also include collecting at least a portion of the first and second beams of light returned from the surface of the specimen. Collecting at least the portion of the first beam of light may include collecting the first beam of light with at least one collector. At least the one collector may include a single dark field collector, a double dark field collector, a near normal dark field collector, or any combination thereof. Collecting at least the portion of the second beam of light may include collecting the second beam of light with at least one collector. At least the one collector may include a single dark field collector, a near normal dark field collector, a bright field collector, or any combination thereof. The method may also include reducing unwanted diffraction orders in the first beam of light scattered from the surface of the specimen and reducing unwanted diffraction orders in the second beam of light scattered from the surface of the specimen.

In an embodiment, the method may include processing the collected portions of the first and second beams of light such that a presence of defects on the specimen can be detected from the collected portions of the first and second beams of light. Defects on the specimen that may be detected from the collected portions of the first and second beams of light may include, for example, defects above the surface of the specimen, defects below the surface of the specimen, defects with varying orientations, or any combination thereof.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
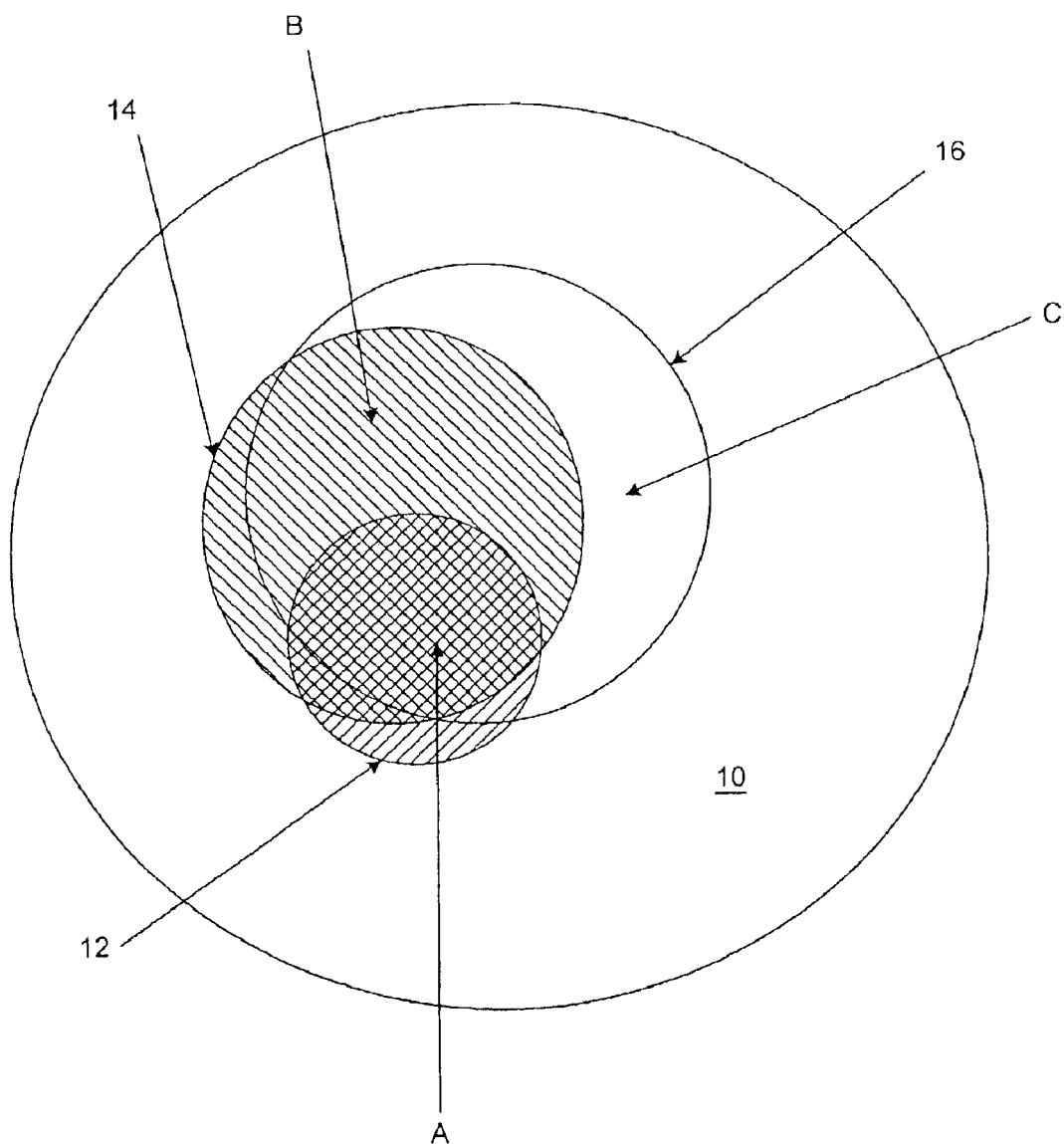
FIG. 1 depicts an embodiment of a Venn diagram describing defects that may be detected by various inspection systems.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Inspection system geometries typically fall into three main categories: bright field, single dark field, and double-dark field. "Bright field" generally refers to a collection geometry configured to collect specularly reflected light from an object. A bright field collection geometry may have any angle of incidence although typically it may have an angle of incidence normal to the object plane.

"Dark field" generally refers to a collection geometry configured to collect only scattered light from an object. The term, however, may also have an additional meaning associated with a surface electromagnetic ("E-M") field of an object. When an incident E-M field has a high reflection coefficient from a surface, approximate cancellation of the incident and reflected waves may produce a reduced E-M field at the surface, which may be commonly referred to as "dark fringe." Similarly, the scattered wave and its reflection can constructively or destructively interfere in the far field.

"Double-dark field" generally refers to an inspection geometry using a steep angle oblique illumination, and a collection angle outside of the plane of incidence. For example, such an arrangement may include a near-grazing illumination angle and a near-grazing collection angle to suppress surface scattering. This suppression occurs because of the dark fringe (also known as the Weiner fringe) near the surface that may occur due to interfering incident and reflected waves. In this manner, the term may be used to designate a system that may be configured for near-grazing incident illumination and near-grazing collection of scattered light.

Typically, no one optical system, including imagers or scanners, in a bright field, dark field, or double dark field geometry, with normal or oblique incidence, will detect all defects. Even if all of the above techniques are combined, some defects may not be detected. In addition, different inspection systems may not detect the same types of defects. For example, turning to the drawings, FIG. 1 illustrates an embodiment of a Venn diagram describing the defects that may be detected by various inspection systems. All defect types may be represented by area 10. Areas 12, 14, and 16 represent portions of all defect types that may be detected by three different types of currently available inspection systems. In this manner, defects in class A may include defect types that may be included in areas 12, 14, and 16. As such, class A defects may be detected by all three different currently available inspection systems. In addition, defects in class B may include defects included in areas 14 and 16, but not in area 12. Therefore, class B defects may be detected by only two of the three different currently available inspection systems. Furthermore, defects in class C may defects in area 16 but not in areas 12 and 14. In this manner, class C defects may be detected by only one of the three different currently available inspection systems. Consequently, an inspection system geometry may be selected depending on, for example, the types of defects that may need to be detected and/or reduced on a specimen. In general, therefore, an inspection system geometry that may detect the largest portion of defects in area 10 may be selected and implemented more often than inspection system geometries that may detect less defects in area 10.

Oblique incidence and normal incidence may have relative areas of strength for defect inspection. Defect inspection, at the front end, involves the processes of light scattering and collection. Therefore, it is the interplay between these two processes that may result in the relative merits of various inspection geometries. Scattering from a specimen such as a wafer upon which integrated circuits ("ICs") may be formed may be estimated using the laws of physics. For example, geometrical arrangement of optical components may determine if a structure or a defect on a specimen is illuminated or if a scattered light collector is sensitive to a presence of a defect on the specimen. Shadowing of a defect either in illumination or collection may cause the sensitivity of an inspection system to the defect to degrade. Near field effects, however, may reduce such shadowing. Therefore, a combination of refracted and reflected light, in addition to incident light, may be taken into consideration to assess an appropriate geometrical arrangement of optical components.

Periodicity of structures on a specimen may also affect light scattering and collection. For example, an IC formed on a wafer may affect the angles at which light may be diffracted from a specimen. Diffraction angles of the diffracted light may be assessed based on Fourier transform techniques. Symmetry may eliminate some diffraction peaks from the diffracted light. In addition, field boundary conditions of an IC structure as a function of input electric field direction may be used to assess input polarization effects. Furthermore, dipoles induced by an incident field may be used to estimate where the scattered field may be weak.

Using the above techniques for assessing scattered light from a specimen, the advantages of different types of illumination may be assessed. For example, using dual incidence provides for the detection of particles and/or defects above a mean surface of a specimen, inspecting rough surfaces, using polarization of the incident light for contrast enhancement, detecting defects below a mean surface of a specimen, scratches, and/or defects with different orientations, inspecting trenches and vias, and bright field collection.

Figure 2:
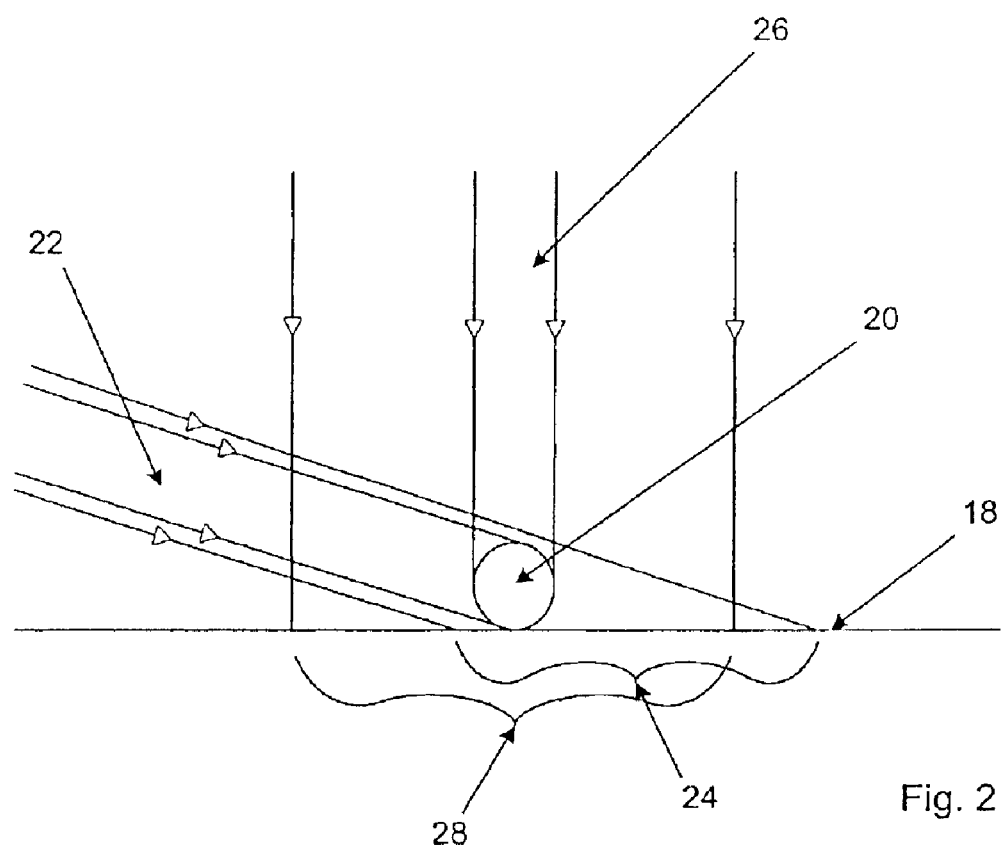
FIG. 2 depicts a schematic view of a surface of a specimen and a particle on the surface illuminated by an oblique incidence beam and a normal incidence beam.

Oblique incidence may be advantageous for detecting particles for at least two separate effects. FIG. 2 is a schematic view of surface 18 of a specimen and particle 20 on the surface illuminated by oblique incidence beam 22. As shown in FIG. 2, oblique incidence beam 22 illuminates an area or spot 24 of surface 20, and a detection system (not shown) may detect light scattered by particle 20 and by spot 24 on surface 18. In addition, as shown in FIG. 2, surface 18 of a specimen and particle 20 on the surface may be illuminated by normal incidence beam 26. As shown in FIG. 2, normal incidence beam 26 may illuminate an area or spot 28 of surface 20, and a detection system (not shown) may detect light scattered by particle 20 on surface 18.

The ratio of the photon flux received by the detector from a particle to that from a spot indicates the sensitivity of the system to particle detection. Therefore, as shown in FIG. 2, a ratio of photon flux from particle 18 to that from the illuminated spot may be greater for oblique illumination. In this manner, for a given throughput, a sensitivity of the oblique incidence beam for detecting particles may be higher than a sensitivity of the normal incidence beam. Regardless of the angle of illumination, an incidence field perceived by particle 18 on specimen 20 may be due to the smallest cross-section of an illumination beam. For a given throughput, therefore, particle 18 receives a greater photon flux from oblique illumination beam 22 than from normal incidence illumination beam 24. Furthermore, throughput may be inversely proportional to the photon flux of the illumination beam. Therefore, because particles may receive a greater photon flux from an oblique illumination beam, an oblique illumination beam may cover a greater surface area on a specimen thereby resulting in a higher throughput.

In addition, oblique incidence may be sensitive to particles due to a vector effect stemming from the interaction of the incident and reflected fields in the vicinity of the surface of the specimen. For S-polarized waves, this interaction may give rise to Wiener fringes, which may have a near-zero amplitude at the surface. The effect of Wiener fringes may be avoided by using P-polarized light, which may result in enhanced sensitivity for small particles. The term "S-polarized" is used to describe the component of polarized radiation having an electrical field which is perpendicular to the plane of incidence of the reflected beam. The term "P-polarized" is used to describe the component of polarized radiation having an electrical field in the plane of incidence of the reflected beam.

Oblique incidence may be advantageous for detecting defects above a mean surface of a specimen due to the inherent nature of large angle oblique incident illumination. For example, the volume of interaction of an oblique illumination field and a sub-surface, or surface breaking, defect may be substantially less than the volume of interaction of an oblique illumination field and a defect above the surface.

As noted above, oblique incidence may be advantageous for inspecting rough films. For example, scattering from a surface of a rough film may display a pronounced angle dependence which may be reduced by steeper illumination and collection angles. In addition, there may be well-defined locations for which certain polarizer/analyzer combinations may result in the suppression of surface scattering. For example, at 90° to the incidence plane, an S to S polarizer/analyzer combination may suppress surface scattering.

Using oblique incidence may be advantageous for using polarization of the incident light for contrast enhancement because the degeneracy that may exist between the S and P polarizations for normal incidence may be substantially eliminated for oblique incidence. Therefore, possibilities such as S-S, P-P, and mixed polarizations may be used with oblique incidence for enhanced inspection of specific sites on a specimen.

An inspection system configured for dual incidence illumination/collection may provide additional capabilities simply because two incidence angles are present. In particular, a greater range of film thicknesses and compositions may be inspected by using dual incidence. This can be very important for inspection of specimens having the AR condition for a particular single incidence angle.

Figure 3:
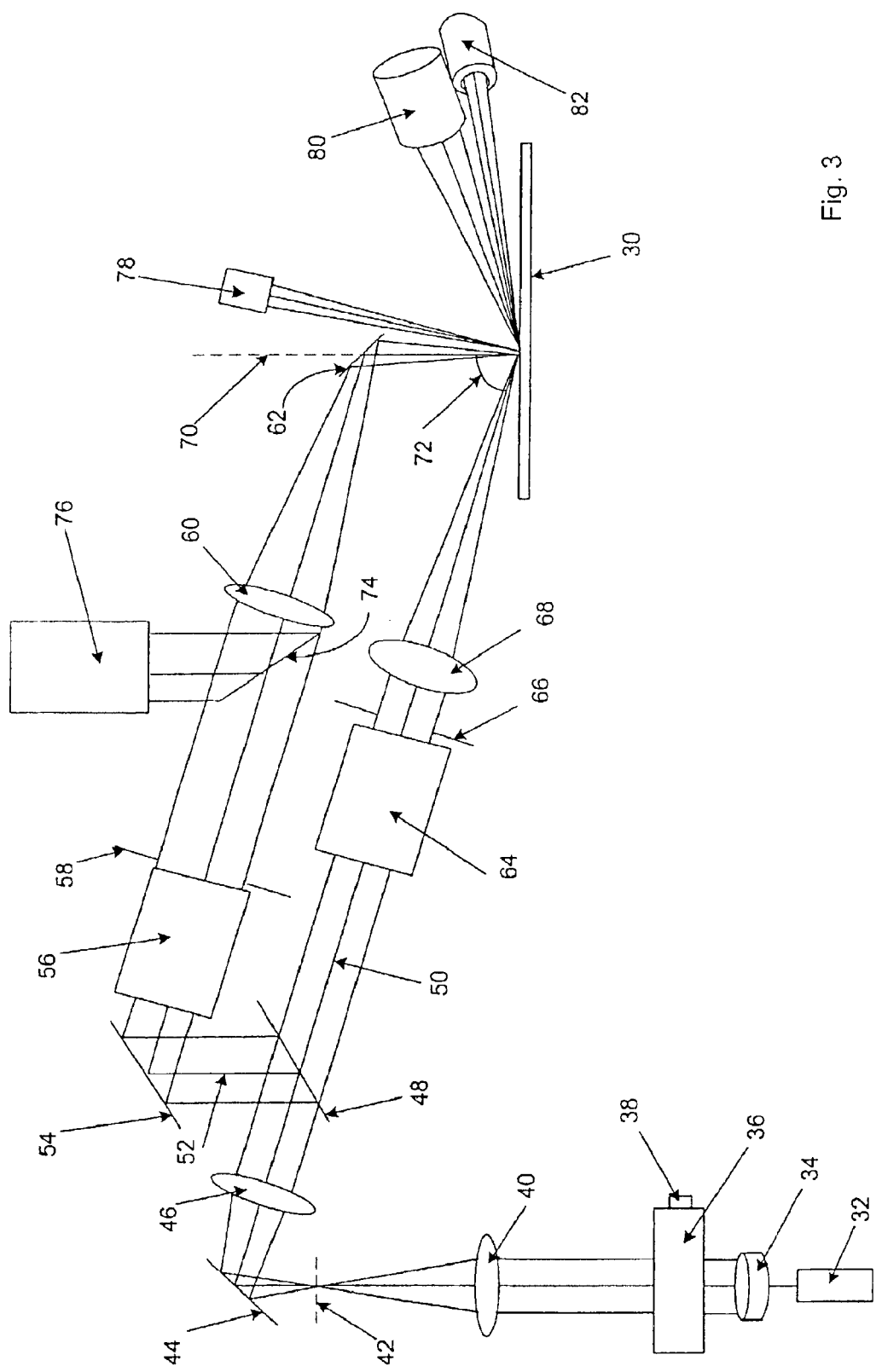
FIGS. 3 and 4 depict partial schematic views of embodiments of a system configured for dual beam illumination of a specimen.

FIG. 3 illustrates a partial schematic view of a system configured for dual beam illumination of specimen 30. The system may include an illumination system. The illumination system may include, for example, light source 32. Light source 32 may be configured to generate a beam of light. For example, light source 32 may be configured to generate a beam of monochromatic light. A suitable monochromatic light source may include, for example, a laser configured to emit light of a known polarization such as a linearly polarized helium neon laser or a solid state laser diode. Such lasers typically may emit light of a single wavelength such as 633 nm and 670 nm, respectively. In addition, a suitable monochromatic light source may include an argon laser or a krypton laser configured to emit light having a wavelength of 488 nm and 647 nm, respectively. Other suitable light sources include, but are not limited to, harmonically generated laser sources, such as frequency doubled Nd-YAG lasers, operating at 532 nm. Furthermore, light source 32 may be configured to generate a beam of broadband light. For example, light source 32 may be configured to a beam of broadband light which may include ultraviolet light, visible light, and/or infra-red light. A suitable broadband light source may include an argon laser or a mixed gas laser configured to generate light in a range of wavelengths from 450 nm to 530 nm and 450 nm to 647 nm, respectively. Furthermore, the system may include multiple light sources. For example, the system may include two lasers. The two lasers may be configured to generate beams of light having substantially different wavelengths.

The illumination system may also include beam expander 34. Beam expander 34 may include, for example, a convex secondary spherical mirror (not shown) and a concave paraboloidal primary mirror (not shown). The beam expander may be configured to direct an entering laser beam to the convex secondary spherical mirror such that the entering laser beam may be expanded. The beam expander may also be configured to direct the expanded beam towards the concave paraboloidal primary mirror such that the expanded beam may be collimated.

The illumination system may also include a light scanning device such as acoustooptical deflector ("AOD") 36. AOD 36 may be configured to direct the generated beam of light at various angles. Deflection of the generated beam of light by AOD 36 may be controlled by a chirp generator (not shown) configured to generate a chirp signal. The chirp signal may be amplified by an amplifier (not shown) and may be applied to transducer 38 coupled to AOD 36. In this manner, a sound wave may be generated to cause deflection of the generated beam of light in a manner known to those skilled in the art. For example, the sound waves generated by transducer 38 may modulate an optical refractive index of an acousto-optic crystal of AOD 36 in a periodic fashion thereby leading to deflection of the generated light beam. The chirp generator may generate appropriate signals such that after being focused by lens 40, deflection of the generated beam of light may cause the focused beam to scan along a scan line such as line 42.

The illumination system may also include folding mirror 44. Folding mirror 44 may be configured to direct the beam of light directed by AOD 36 to lens 46. Lens 46 may include, for example, a collimating lens or a relay lens. Lens 46 may be configured to direct the beam of light to beam splitting device 48. Beam splitting device 48 may be configured to split the directed beam of light into first beam of light 50 and second beam of light 52. Beam splitting device 48 may be actuated. For example, the beam splitting device may be actuated by miniaturized mechanical systems such as piezoelectric actuators. Alternatively, the beam splitting device may be electrostatically actuated by electrodes located on either side of the beam splitting device.

Beam splitting device 48 may be a dichroic beam splitter. In this manner, first beam of light 50 and second beam of light 52 may have substantially different wavelengths. In addition, beam splitting device 48 may be a polarizing beam splitter. In this manner, first beam of light 50 and second beam of light 52 may have substantially different polarizations. For example, a polarization of first beam of light 50 may be substantially orthogonal to a polarization of second beam of light 52. Alternatively, a half-wave plate (not shown) may be positioned between beam splitting device 48 and a surface of specimen 30 in a path of first beam of light 50 or second beam of light 52. The half-wave plate may be configured to alter a polarization of the first beam of light or the second beam of light. For example, the half-wave plate may be configured to alter a polarization of the first beam of light such that the polarization of the first beam of light may be substantially orthogonal to the second beam of light, or vice versa.

In addition, beam splitting device 48 may be configured such that a portion of the beam of light transmitted by the beam splitting device may be larger than a portion of the beam of light reflected by the beam splitting device. In this manner, an intensity, or a power, of the second beam of light may be substantially less than an intensity of the first beam of light. Alternatively, an additional optical component may be arranged in a path of second beam of light 52. The additional optical component may be configured to reduce an intensity of the second beam of light relative to the first beam of light.

The illumination system may also include folding mirror 54. Folding mirror 54 may be positioned in a path of second beam of light 52 such that the second beam of light may be directed from beam splitting device 48 to magnification changer 56. Magnification changer 56 may be configured to alter a magnification of second beam of light 52 by about 1×, about 0.8×, or about 0.7×. An appropriate magnification changer may vary depending on, for example, a selected spot size of second beam of light 52 on specimen 30. A Gaussian filter (not shown) may be coupled to magnification changer 56. The Gaussian filter may include, for example, a one-dimensional amplitude filter with a Gaussian attenuation along the shorter length. Alternatively, a Gaussian filter may be positioned at the aperture of objective lens 60, as described herein. The illumination system may also include spatial filter 58 configured to alter a cross-sectional area of second beam of light 52 exiting magnification changer 56. For example, spatial filter 58 may be made of a substantially opaque material having a central opening or aperture through which at least a portion of second beam of light 52 may pass. In addition, the illumination system may include objective lens 60. Objective lens 60 may have an effective focal length ("EFL") of approximately 76 mm. The illumination system may also include folding mirror 62 configured to direct the second beam of light focused by objective lens 60 to a surface of specimen 30 at a substantially normal angle.

Beam splitting device 48 may be configured to direct first beam of light 50 to magnification changer 64. Magnification changer 64 may be configured to alter a magnification of first beam of light 50 by about 1×, about 1.4×, or about 2×. As described above, an appropriate magnification changer may vary depending on, for example, a selected spot size of first beam of light 50 on specimen 30. The illumination system may also include spatial filter 66 configured to alter a cross-sectional area of first beam of light 50 exiting magnification changer 64. Spatial filter 66 may be configured as described herein. In addition, the illumination system may include objective lens 68. Objective lens 68 may be identical to objective lens 60 positioned in a path of second beam of light 52. The illumination system may be configured such that the first beam of light focused by objective lens 68 may be directed to a surface of specimen at an oblique angle of incidence. The oblique angle of incidence may be measured from axis 70 substantially perpendicular to an upper surface of specimen 30. As shown in FIG. 3, oblique angle of incidence 72 may include an angle of incidence from approximately 5° to approximately 80°, as measured from axis 70. For example, oblique angle of incidence 72 may be approximately 70°, as measured from axis 70.

Figure 4:
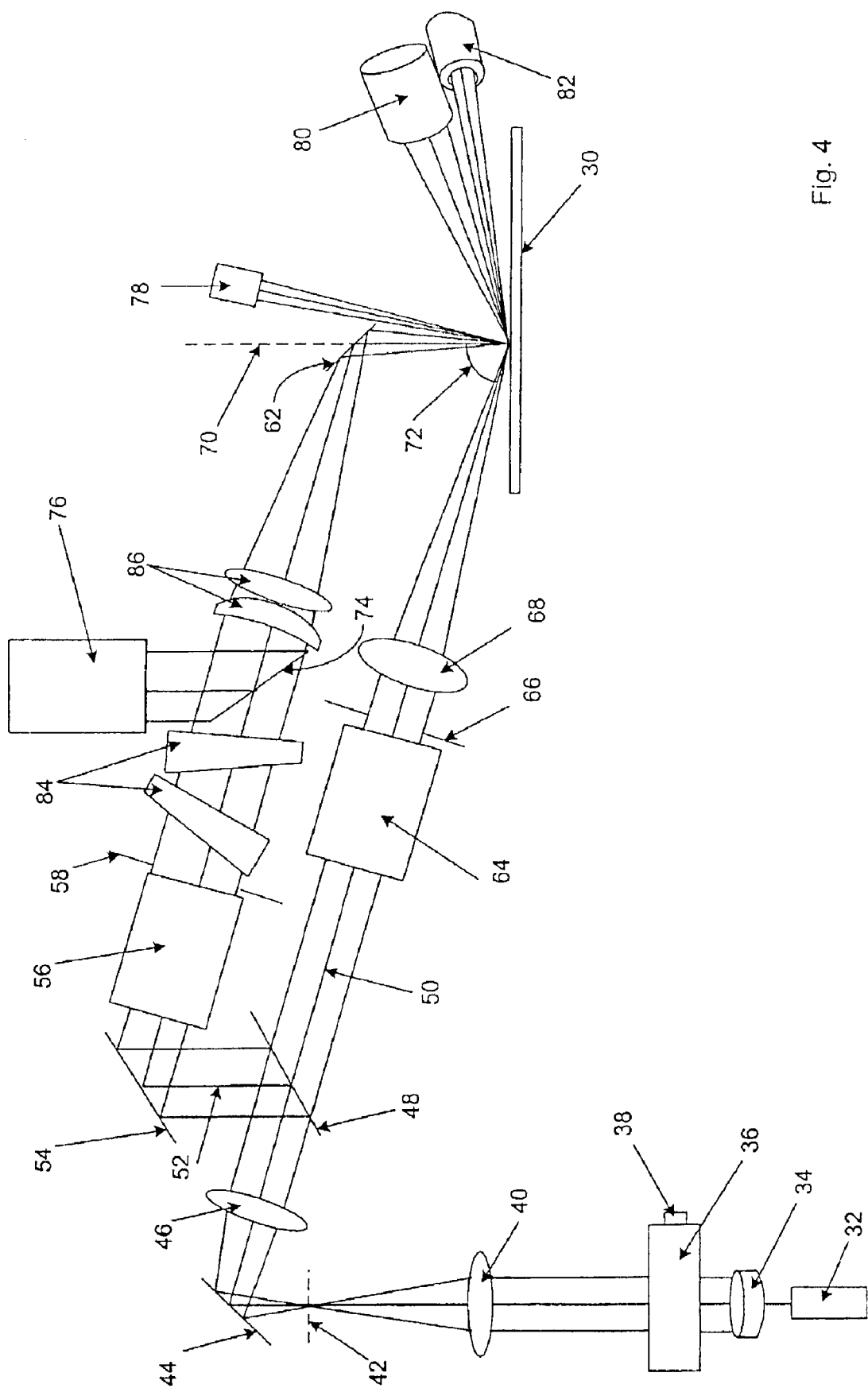

FIG. 4 illustrates another embodiment of the system as illustrated in FIG. 3 that includes additional optical components. For example, as shown in FIG. 4, the illumination system may include pair of anamorphic prisms 84. Pair of anamorphic prisms 84 may be positioned in a path of second beam of light 52. The pair of anamorphic prisms may be configured to reduce a diameter of the second beam of light in one direction such that a shape of the second beam of light incident on the surface of specimen 30 may be substantially the same as a shape of the first beam of light incident on the surface of specimen 30. For example, a normal incidence beam may ordinarily have a round spot whereas the obliquity factor produces an elliptical spot for an oblique incidence beam. Therefore, the obliquity factor that exists in the oblique beam of light may be simulated in the normal beam of light using anamorphic prisms, which may also be commonly referred to as an anamorphic telescope. In this manner, the beam diameter of the normal beam of light may be reduced in one direction before the final objective thereby enlarging focal distribution along this length. As such, an entire area of the first beam of light incident upon the surface of the specimen may overlap substantially an entire area of the second beam of light incident upon the surface of the specimen.

As shown in FIG. 4, the illumination system may also include focusing lens 86. Focusing lens 86 may be positioned in a path of second beam of light 52 in a non-telecentric geometry. In this manner, the focusing lens may be configured to increase the telecentricity of the second beam of light. For example, a geometrical distance between specimen 30 and beam splitter 48 in a normal incidence path may be different from that in the oblique incidence path. In the oblique incidence path, for telecentric scanning, the position of the scanning pivot is at the back focal plane of the focusing lens. Thus, telecentricity may not be satisfied in the normal incidence path. However, for a focal spot size that may not be relatively small, using focusing lens 86 in a non-telecentric geometry may introduce negligible aberrations in the focal point for reasonable departures from telecentricity. For example, if the scanning pivot is at 2f from the lens, rather than f, the spot size may be almost identical to that in the telecentric case. Focusing lens 86 may replace objective lens 60, as shown in FIG. 4, or may be positioned in a path of second beam of light 52 in addition to objective lens 60. Focusing lens 86 may include a combination of a variety of individual lenses.

Typically, a path between a folding mirror and a surface of a specimen along an oblique incidence direction is shorter than any other path between the folding mirror and the surface of the specimen, particularly along the normal incidence direction. The illumination system may be arranged, however, such that an oblique incidence path from a light source and a specimen may be approximately equal to a normal incidence path. For example, the illumination system may be arranged in a quadrangle geometrical arrangement. In this manner, folding mirror 54 may be at one corner of the quadrangle and specimen 30 may be at the other corner of the quadrangle. The oblique and normal incidence paths, then, are the two path along the sides of the quadrangle. Such a geometrical arrangement may be commonly referred to as a "Mach-Zehnder" type of arrangement.

The system may also include a collection system. For example, the collection system may be configured to collect at least a portion of the first beam of light returned from the surface of the specimen and to collect at least a portion of the second beam of light returned from the surface of the specimen. For example, as shown in FIGS. 3 and 4, second beam of light 52 may be specularly reflected from the surface of specimen 30. Specularly reflected light may pass back through objective lens 60. The system may also include reflective beam splitter 74. Reflective beam splitter 74 may be positioned in a path of second beam of light 52. Reflective beam splitter 74 may be configured such that second beam of light 52 directed to a surface of specimen 30 may be substantially unaltered by reflective beam splitter. Reflective beam splitter 74 may also be actuated as described herein. Reflective beam splitter 74 may also be configured to direct at least a portion of second beam of light 52 specularly reflected from the surface of specimen 30 to collector 76 of the collection system. Collector 76 may include, but may not be limited to, an imaging lens, a cylindrical lens, a relay lens, and/or a collimating lens. In this manner, collector 76 may be configured to collect light propagating from a surface of specimen 30 along a bright field path.

Light collected by collector 76 may provide information on reflectance variation, which may be indicative of possible process variation, and flat and weakly scattering defects. In addition, light collected by collector 76 may be used for pattern recognition. Furthermore, light collected by collector 76 may provide information such that different defects detected on specimen 30 may be classified. For example, light collected by collector 76 may be used to generate a signal. Such a signal may be correlated to a known type of defect if a defect on the specimen may have been characterized by another analytical technique known in the art. In this manner, a generated signal may be compared to signals of known types of defects to assess the type of defect that may be present on a specimen.

The collection system may also include additional collectors as described herein. For example, second beam of light 52 may also be scattered from a surface of specimen 30. Scattered portions of second beam of light 52 may be collected by near specular dark field collector 78. Near specular dark field collector 78 may be positioned at an elevational angle of approximately 70° to approximately 85°, as measured from a surface of the specimen. In addition, near specular dark field collector 78 may be positioned at any azimuth angle, which may be measured as described herein. Near specular dark field collector 78 may be configured as described above.

Near specular dark field collector 78 may also include a lens having a size large enough to accommodate angles outside the range dictated by the illumination numerical aperture ("NA"). Alternatively, near specular dark field collector 78 may be coupled to a separate lens with a Fourier transform spatial filter over the region of the separate lens not covered by the scanned field. The spatial filter may be, for example, a liquid crystal ("LC") based system or a wire structure. Scattered portions of first beam of light 50 may also be collected by near specular dark field collector 78.

Figure 5:
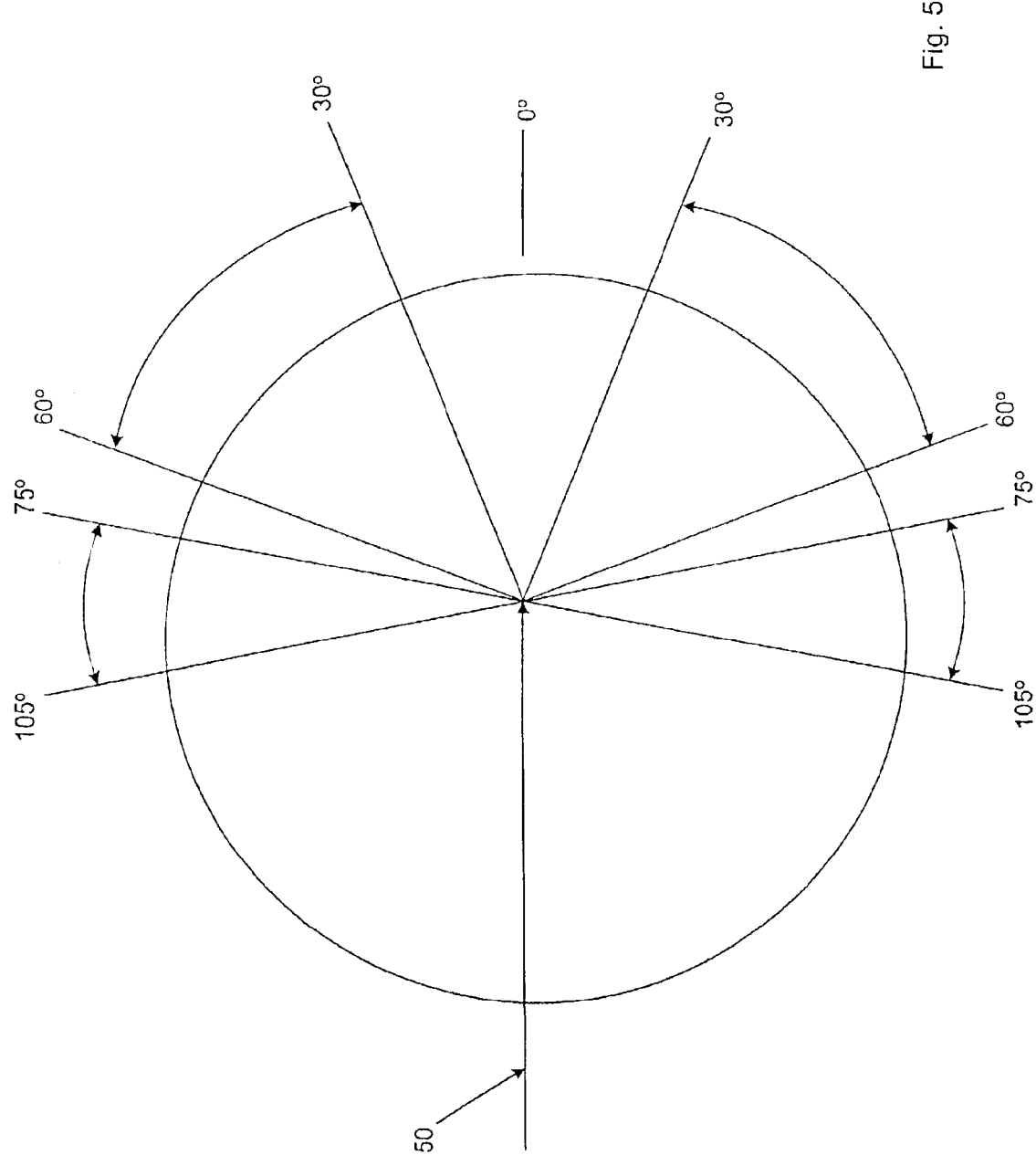
FIG. 5 depicts a plan view of an embodiment of azimuthal positions of collectors with respect to an oblique incidence beam.

The collection system may also include side collector 80. Side collector 80 may be configured as a single dark field collector. For example, side collector 80 may be configured to detect dark field light propagating from a surface of specimen 30. In this manner, side collector 80 may be configured to collect a portion of first light beam 50 scattered from the surface of specimen 30 or a portion of second beam of light 52 scattered from the surface of specimen 30. Side collector 80 may be further configured as described above. Side collector 80 may be positioned at an elevational angle of approximately 5° to approximately 60°, as measured from a surface of specimen 30. In addition, side collector 80 may be positioned at an azimuth angle of approximately 30° to approximately 60°. Alternatively, side collector 80 may be positioned at an azimuth angle of approximately 75° to approximately 105°. FIG. 5 illustrates examples of possible azimuth angles of side collector 80 with respect to first beam of light 50. An azimuth angle may be measured from a position on a specimen as indicated by 0° in FIG. 5. Combinations of these collection spaces, as well as other suitable combinations are considered within the scope of this invention.

The collection system may also include a number of other collectors such as side collector 82. Side collector 82 may also be configured as described above. Side collector 80 and side collector 82, however, may have substantially different arrangements within the system. For example, side collector 80 and side collector 82 may be positioned at substantially different elevational angles and/or at substantially different azimuth angles. In this manner, different types of scattered and/or reflected light may be detected by each of the side collectors. For example, side collector 82 may be configured as a single dark field detector and side collector 80 may be configured as a double dark field detector.

The collection system may also include a spatial filter (not shown) configured to reduce unwanted diffraction orders in the first beam of light scattered from the surface of the specimen and to reduce unwanted diffraction orders in the second beam of light scattered from the second beam of light scattered from the surface of the specimen. Such a spatial filter may be coupled to each detector described herein. For example, repetitive pattern structures on the specimen may produce unwanted diffraction orders in the first or second beam of light scattered from the surface of the specimen.

The Fourier transform generated by the normal and oblique beams of light may have the same form, but may be shifted with respect to each other in one direction. For example, the oblique incidence beam may be viewed as a normal incidence beam with a linear ramp phase shift across it. Due to the shifting theorem of Fourier transform, the transform domain may be shifted in the fx direction. Thus, if the spatial filter used has stripes to negate the fx direction, the same filter may operate identically for both illuminations. A spatial filter that may be used for oblique and normal incidence simultaneous illumination may have a greater number of OFF stripes than a spatial filter used for sequential illumination in order to cancel the unwanted orders due to both illumination modes.

Light collected by collectors of the collection system may be directed to a detection system (not shown). The detection system may be configured to process the collected portions of the first and second beams of light such that a presence of defects on the specimen can be detected from the collected portions of the first and second beams of light. For example, a detection system may include any light sensitive device including imaging and non-imaging devices known in the art such as a pattern recognition device, a charge coupled device ("CCD") camera, a video camera, a split photodiode detector, a photomultiplier tube ("PMT"), a conventional spectrophotometer, a quad-cell detector, a linear sensor array, and a position sensitive detector. The light sensitive device may generate an analog signal in response to detected light.

The generated signal may digitized by an analog/digital converter (not shown) coupled to the light sensitive device, and the digital data may be sent through an interface to a processing device (not shown) such as an image processing device coupled to the system. An image processing device may be a parallel processing system that may be commonly used by the machine vision industry. The image processing device may be configured to generate an image of the illuminated area of specimen 30. The image processing device may also be coupled to a host computer that may be configured to control the system and to perform data processing functions. For example, data processing functions may include determining a presence of defects on a surface of a specimen by comparing output signals of light sensitive devices generated from illuminating two different locations on the specimen. Two different locations on the specimen may include, for example, two dies of a semiconductor wafer. Defects on the specimen that can be detected from the collected portions of the first and second beams of light may include defects above the surface, defects below the surface, defects with varying orientations, or any combination thereof.

Figure 6:
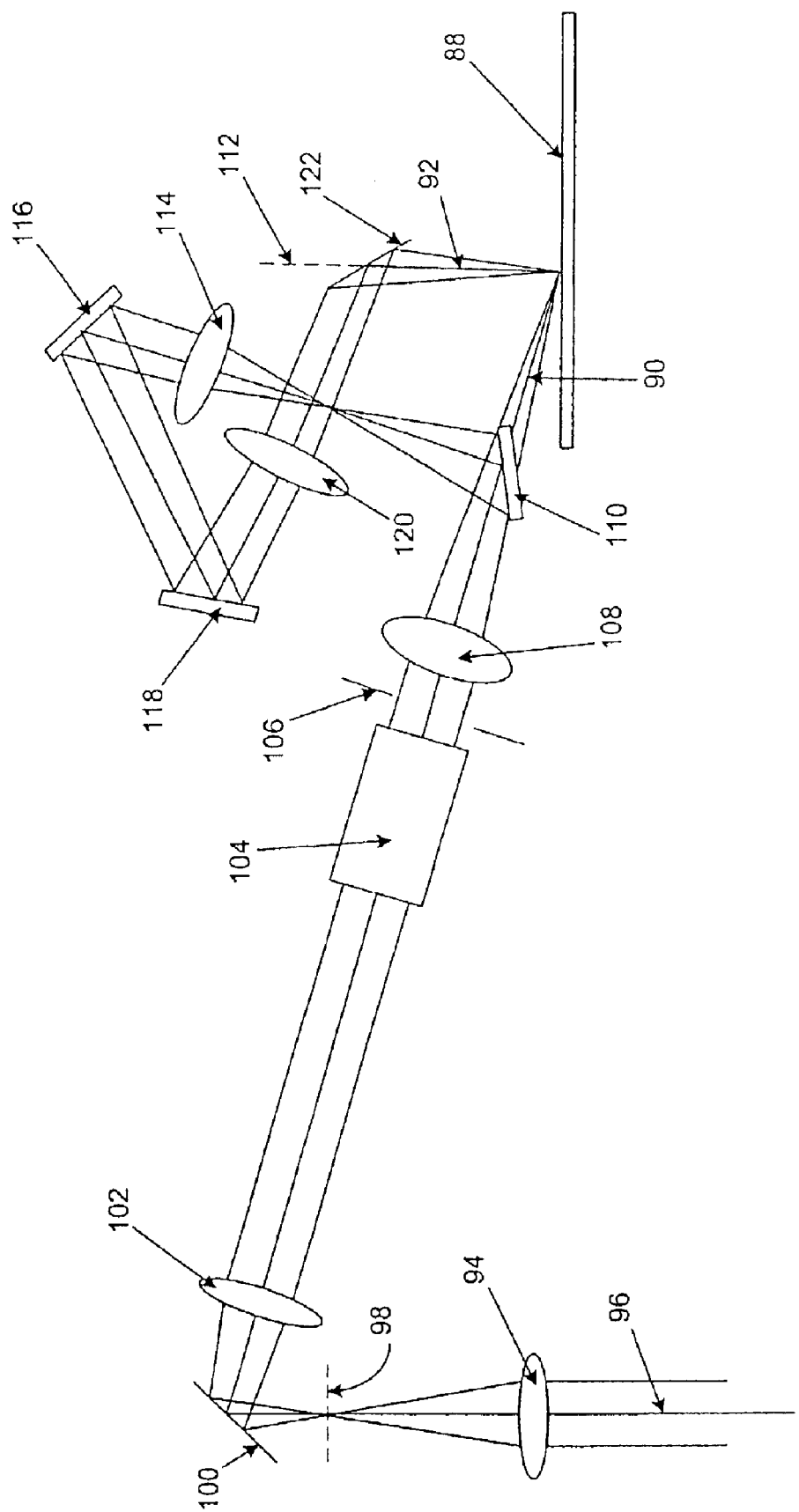
FIGS. 6 and 7 depict partial schematic views of alternate embodiments of a system configured for dual beam illumination of a specimen.

FIG. 6 illustrates a partial schematic view an alternate embodiment of a system configured for dual beam illumination of specimen 88. The system may include an illumination system configured to direct first beam of light 90 to a surface of specimen 88 at an oblique angle of incidence and to direct second beam of light 92 to a surface of the specimen at a substantially normal angle. The illumination system may include lens 94. Lens 94 may be configured to receive light 96 that may have been generated by a light source (not shown). The light source may be configured as described herein. In addition, light 96 may have been expanded by a beam expander (not shown) as described herein. Light 96 may also have been directed at various angles by a light scanning device (not shown) as described herein. Lens 94 may be configured to focus light 96 to focal plane 98. Lens 94 may also be configured such that the focused light may be directed to folding mirror 100. Folding mirror 100 may be configured to direct the beam of light to lens 102. Lens 102 may be configured to direct the beam of light to magnification changer 104. Magnification changer 104 may be configured to alter a magnification of the beam of light by about 1×, about 1.4×, or about 2×.

The illumination system may also include spatial filter 106 configured to alter a cross-sectional area of the beam of light exiting the magnification changer. The spatial filter may be configured as described herein. In addition, the illumination system may include objective lens 108. The illumination system may also include beam splitting device 110. Beam splitting device 110 may be configured as described above. For example, beam splitting device 110 may be configured to separate light from objective lens 108 into first beam of light 90 and second beam of light 92. The illumination system may be configured such that first beam of light 90 may be directed from beam splitting device 110 to a surface of specimen 88 at an angle of incidence from about 5° to about 80°, as measured from axis 112 normal to an upper surface of specimen 88. For example, first beam of light 90 may be directed to a surface of specimen 88 at an angle of incidence of approximately 70°. Second beam of light 92 may be directed from beam splitting device 110 to lens 114, to a series of folding mirrors, 116, 118, and to lens 120. Second beam of light 92 may be directed from lens 120 to folding mirror 122 such that second beam of light 92 may be directed to a surface of specimen 88 at a substantially normal angle. The system may also be further configured as described herein.

Figure 7:
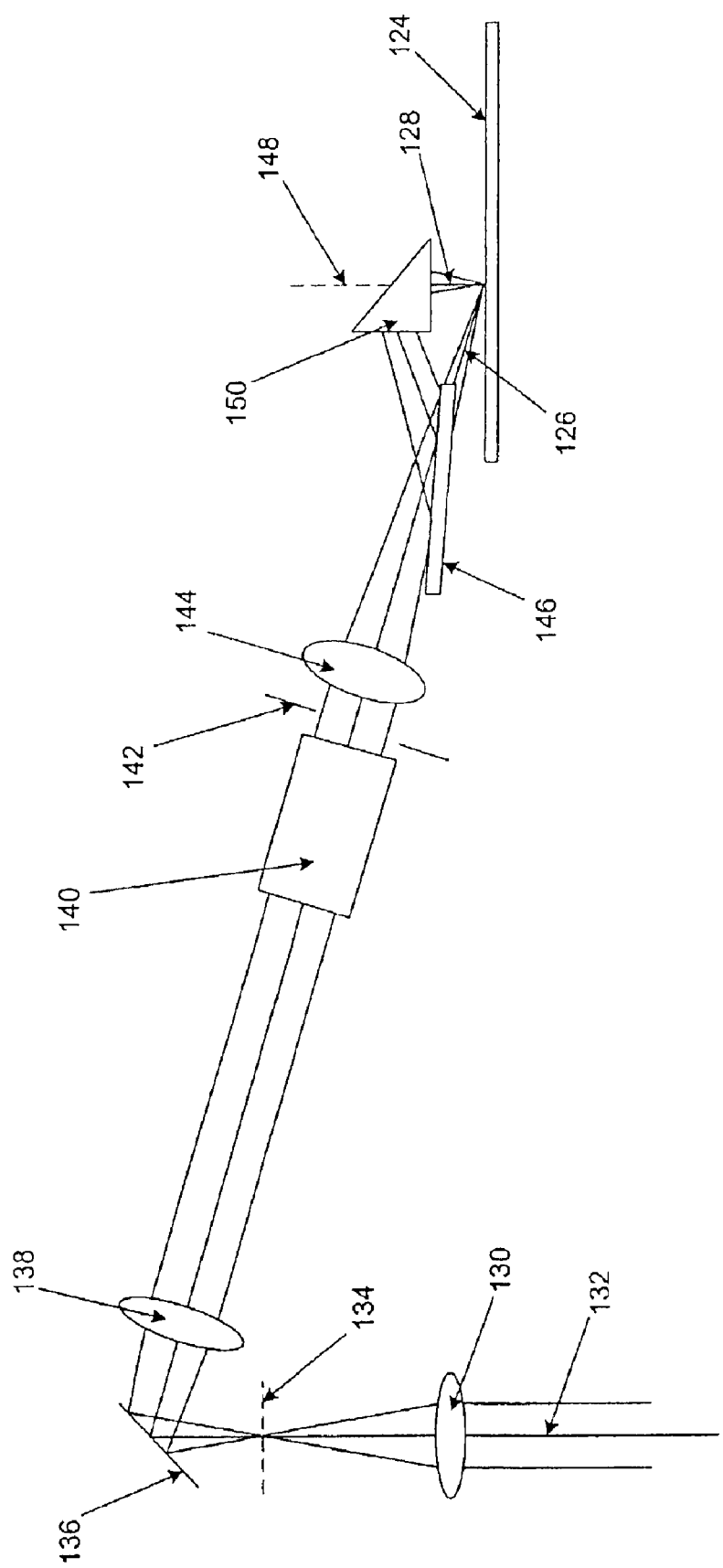

FIG. 7 illustrates a partial schematic view an alternate embodiment of a system configured for dual beam illumination of specimen 124. The system may include an illumination system configured to direct first beam of light 126 to a surface of specimen 124 at an oblique angle of incidence and to direct second beam of light 128 to a surface of the specimen at a substantially normal angle. The illumination system may include lens 130. Lens 130 may be configured to receive light 132 that may have been generated by a light source (not shown). The light source may be configured as described herein. In addition, light 132 may have been expanded by a beam expander (not shown) as described herein. Light 132 may also have been directed at various angles by a light scanning device (not shown) as described herein. Lens 130 may be configured to focus light 132 to focal plane 134. Lens 130 may also be configured such that the focused light may be directed to folding mirror 136. Folding mirror 136 may be configured to direct the beam of light to lens 138. Lens 138 may be configured to direct the beam of light to magnification changer 140. Magnification changer 140 may be configured as described herein.

The illumination system may also include spatial filter 142 configured to alter a cross-sectional area of the beam of light exiting the magnification changer. The spatial filter may be configured as described herein. In addition, the illumination system may include objective lens 144. Objective lens 144 may be configured as described herein. The illumination system may also include beam splitting device 146. Beam splitting device 146 may be configured as described above. For example, beam splitting device 146 may be configured to separate light from objective lens 144 into first beam of light 126 and second beam of light 128. The illumination system may be configured such that first beam of light 126 may be directed from beam splitting device 146 to a surface of specimen 124 at an angle of incidence from about 5° to about 80°, as measured from axis 148 normal to an upper surface of specimen 124. For example, first beam of light 126 may be directed to a surface of specimen 124 at an angle of incidence of approximately 70°. Second beam of light 128 may be directed from beam splitting device 146 to prism 150 such that second beam of light 128 may be directed to a surface of specimen 124 at a substantially normal angle. The system may also be further configured as described herein.

A system as described herein may be operated with simultaneous dual beam illumination for a number of reasons. For example, spot sizes of the oblique incidence beam and the substantially normal incidence beam may be approximately equal (i.e., matched to about ½ pixel size). In addition, a spatial filter, as described herein, may be configured to accommodate two illuminations having substantially different angles of illumination simultaneously. Furthermore, polarization of the two beams may be orthogonal, which can always be arranged, because normal incidence may be relatively unaffected (to the first order) by polarization. Therefore, polarization of the normal incidence illumination beam may be set orthogonally to that of the oblique incidence beam, which may vary depending on, for example, defects of interest and characteristics of the specimen being inspected. Dual beam illumination may also be used if the level of speckle generated by the presence of the normal incidence is not excessive.

The system may also be operated with simultaneous dual beam illumination if characteristics of the sample warrant dual beam illumination. For example, dual beam illumination may be appropriate if a specimen may not be inordinately made of rough films, which may render the normal incidence beam substantially useless. In addition, dual beam illumination may provide greater flexibility to inspect dielectric films. Furthermore, the system may be operated with simultaneous dual beam illumination if on-the-fly classification of defects may not be required. For example, if review and classification of defects may be performed, then the two incidence beams may be separated in time domain (e.g., through AC modulation).

Regardless of whether the system may be operated simultaneously or sequentially, at least a small portion of the normal incidence beam may always be incident upon a specimen to provide bright field data. For example, a small portion of the normal incidence beam may include about 1/100 to about 1/1000 of the normal incidence beam energy. The illumination level of the normal incidence beam may vary depending on, for example, a configuration of the spatial filter. For example, if the spatial filter is configured for oblique illumination, the level of the normal incidence illumination may be lower than that of the oblique incidence beam by a ratio comparable to the extinction coefficient afforded by the spatial filter. If normal incidence illumination exceeds this level, a sizable normal-induced unwanted diffraction order may enter the detectors.

The system may also be operated such that the oblique incidence beam and the substantially normal incidence beam may illuminate a specimen sequentially. During such operation, a bright field signal may be obtained throughout inspection despite the relatively strong bright field signal. For example, if the bright field detector is a PMT, then the specularly reflected normal incidence beam may be attenuated to avoid PMT saturation effects. In this manner, if only normal incidence illumination is used, then the bright field PMT may be used at a relatively low gain (drive voltage). When the primary beam is to be an oblique incidence beam, then most of the input light may be directed toward the oblique incidence path, and only a relatively small fraction of the light may be directed toward the normal incidence path. As a result, there may be relatively low excess speckle noise due to the normal illumination of rough films at the dark field detector. Such a small amount of normal illumination, however, may be sufficient, in combination with a synchronized increase in the PMT gain, to produce an excellent bright field image. As such, although the dark field signal may be obtained at times from the oblique incidence light and at times from the normal incidence light, the bright field image may always be obtained. Therefore, an advantage of dual beam illumination may be that switching power between the two illuminations as described above may be eliminated.

As described herein, a system may be configured to use the same light scanning device (e.g., an AOD) to have a simultaneous multi-perspective inspection of a specimen. In particular, a system may be configured to use a single fast AOD for two widely varying illumination beams. The use of a single AOD may provide precise repeatability of the fast scanning action at different times. Alternatively, the system may include two separate light scanning devices (i.e., a light scanning device for each illumination path) with dedicated optics. In either case, the system may be configured such that a first beam of light and a second beam of light may scan the specimen substantially simultaneously. In this manner, a final throughput of the system may not be reduced due to the multi-perspective inspection capability. Alternatively, a system may be configured to operate the beam separately, for specific cases. In addition, due to the design of the optical paths, a single magnification changer may be used to alter a spot size of multiple light beams directed at various angles.

A system, as described herein, may be used for various modes of operation. For example, the system may be used for oblique illumination only with collection using side and near-normal collectors. In addition, the system may be used for normal illumination only with collection using side, near-normal, and bright field collectors. The system may also be used for simultaneous normal and oblique illumination, which may have orthogonal polarizations, with collection using a spatial filter as described herein with side, near-normal, and bright field collectors. Alternatively, the system may be used for oblique and simultaneous reduced power, normal illumination with collection using side, near-normal and bright field collectors.

The beams that may be incident upon the specimen during inspection may be determined by the inspection application. For example, the beams that may be incident upon a specimen during inspection may be determined by characteristics of a specimen, defects which may be present on a specimen, and defects which may be of interest.

In addition, the beams of light that may be incident upon a specimen during inspection may be further determined using the advantages of various types of illumination as described above. Therefore, by providing different collection configurations, a system as described herein may provide optimization of a specific combination of illumination and collection for a specific type of defect. As described above, the system may be configured to direct the first and second beams of light to the specimen substantially simultaneously or sequentially. Therefore, if the oblique angle of incidence is substantially different than the substantially normal angle of incidence, then a system as described herein may have a larger capture rate for a larger number of types of defects than a single illumination system.

Figure 8:
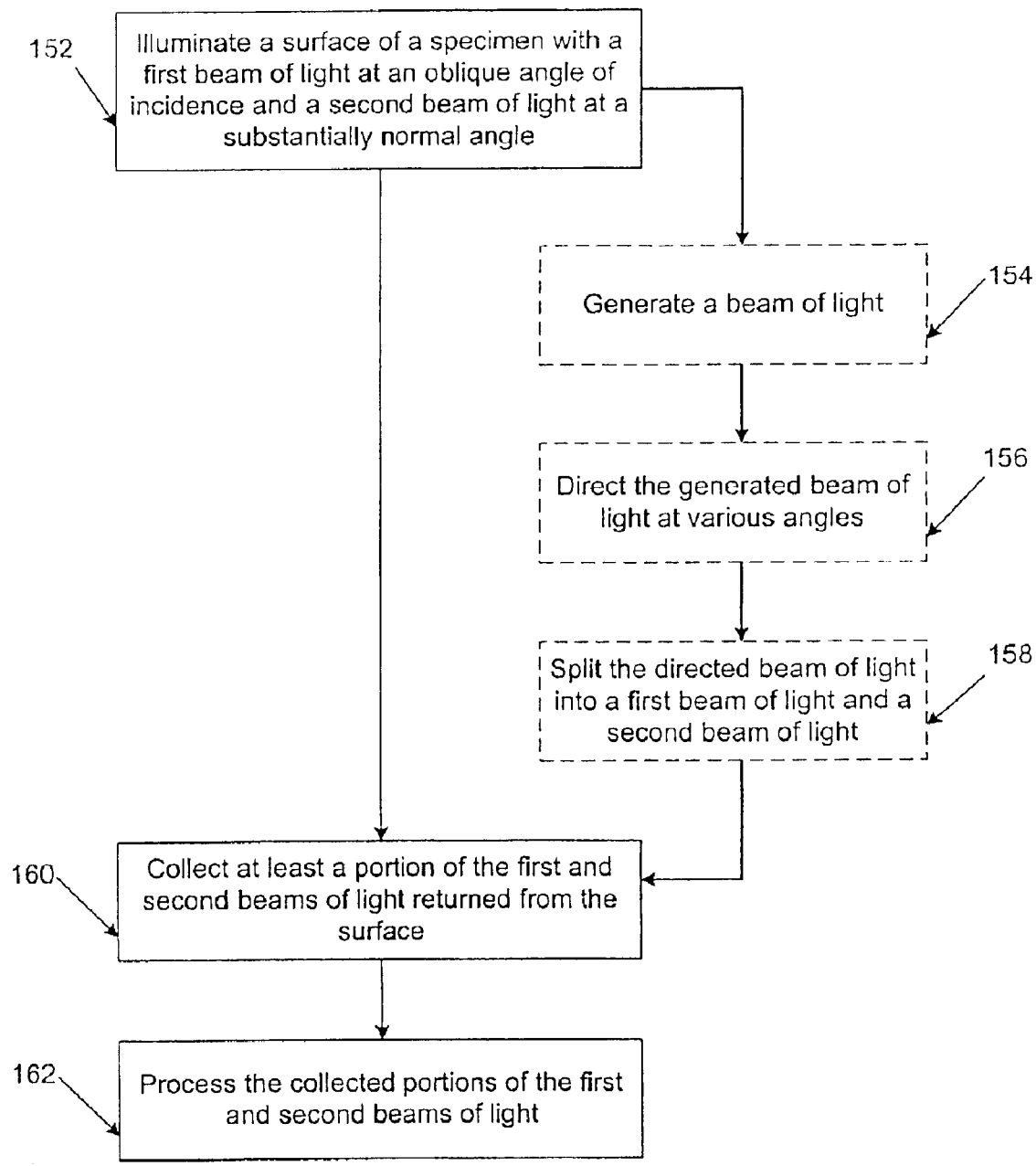
FIG. 8 depicts a flow chart of an embodiment of a method for inspecting a specimen.

FIG. 8 illustrates an embodiment of a method for inspecting a specimen. The specimen may include, for example, a wafer that may be used for semiconductor fabrication. The method may include illuminating a surface of the specimen with a first beam of light at an oblique angle of incidence and with a second beam of light at a substantially normal angle, as shown in step 152. The oblique angle of incidence may include an angle of incidence from approximately 5° to approximately 80°. For example, the oblique angle of incidence may be approximately 70°. A polarization of the first beam of light may be substantially orthogonal to a polarization of the second beam of light. In addition, an intensity of the second beam of light may be substantially less than an intensity of the first beam of light. Furthermore, substantially an entire area of the first beam of light incident upon the surface of the specimen may overlap substantially an entire area of the second beam of light incident upon the surface of the specimen.

Illuminating a surface of the specimen may include generating a beam of light, as shown in step 154. Illuminating a surface of the specimen may also include directing the generated beam of light at various angles, as shown in step 156. In addition, illuminating a surface of the specimen may include splitting the directed beam of light into the first beam of light and the second beam of light, as shown in step 158. Illuminating the surface of the specimen may include illuminating the surface of the specimen with the first beam of light and the second beam of light substantially simultaneously. Alternatively, illuminating the surface of the specimen may include illuminating the surface of the specimen with the first beam of light and the second beam of light sequentially.

In addition, illuminating the surface of the specimen may include reducing a diameter of the second beam of light in one direction such that a shape of the second beam of light incident on the surface of the specimen may be substantially the same as a shape of the first beam of light incident on the surface of the specimen. Illuminating the surface of the specimen may also include increasing a telecentricity of the second beam of light with a focusing lens in a non-telecentric geometry positioned in a path of the second beam of light. Furthermore, illuminating the surface of the specimen may include illuminating the surface of the specimen with an illumination system arranged in a Mach-Zehnder type arrangement.

The method may also include collecting at least a portion of the first and second beams of light returned from the surface of the specimen, as shown in step 160. Collecting at least the portion of the first beam of light may include collecting the first beam of light with at least one collector. At least the one collector may include, but may not be limited to, a single dark field collector, a double dark field collector, a near normal dark field collector, or any combination thereof. In addition, collecting at least the portion of the second beam of light may include collecting the second beam of light with at least one collector. At least the one collector may include, but may not be limited to, a single dark field collector, a near normal dark field collector, a bright field collector, or any combination thereof. The method may also include reducing unwanted diffraction order in the first beam of light scattered from the surface of the specimen and in the second beam of light scattered from the surface of the specimen.

The method may further include processing the collected portions of the first and second beams of light such that a presence of defects on the specimen can be detected from the collected portions of the first and second beams of light, as shown in step 162. Defects on the specimen that may be detected from the collected portions of the first and second beams of light may include defects above the surface, defects below the surface, defects with varying orientations, or any combination thereof.

Further modifications and alternative embodiments of various aspects of the invention may be apparent to those skilled in the art in view of this description. For example, a system that may be configured to inspect a specimen may include simultaneous or sequential multi-angle illumination is provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to inspect a specimen during use, comprising:
    an illumination system configured to direct a first beam of light to a surface of the specimen at an oblique angle of incidence during use and to direct a second beam of light to the surface of the specimen at a substantially normal angle during use, wherein an intensity of the second beam of light is substantially less than an intensity of the first beam of light, and wherein the illumination system comprises:
        a light source configured to generate a beam of light during use;
        a light scanning device configured to direct the generated beam of light at various angles during use; and
        a beam splitting device configured to split the directed beam of light into the first beam of light and the second beam of light during use;
    a collection system configured to collect at least a portion of the first beam of light returned from the surface of the specimen during use and to collect at least a portion of the second beam of light returned from the surface of the specimen during use; and
    a detection system configured to process the collected portions of the first and second beams of light such that a presence of defects on the specimen can be detected from the collected portions of the first and second beams of light.

2. The system of claim 1, wherein the illumination system is further configured to direct the first and second beams of light to the surface of the specimen substantially simultaneously.

3. The system of claim 1, wherein the illumination system is further configured to direct the first and second beams of light to the surface of the specimen sequentially.

4. The system of claim 1, wherein the light scanning device comprises an acousto-optical deflector.

5. The system of claim 1, wherein the illumination system further comprises a pair of anamorphic prisms positioned in a path of the second beam of light, and wherein the pair of anamorphic prisms is configured to reduce a diameter of the second beam of light in one direction during use such that a shape of the second beam of light incident on the surface of the specimen is substantially the same as a shape of the first beam of light incident on the surface of the specimen.

6. The system of claim 1, wherein the illumination system further comprises a focusing lens in a non-telecentric geometry positioned in a path of the second beam of light, and wherein the focusing lens is configured to increase the telecentricity of the second beam of light during use.

7. The system of claim 1, wherein the illumination system is arranged in a Mach-Zehnder type arrangement.

8. The system of claim 1, wherein a polarization of the first beam of light is substantially orthogonal to a polarization of the second beam of light.

9. The system of claim 1, wherein substantially an entire area of the first beam of light incident upon the surface of the specimen overlaps substantially an entire area of the second beam of light incident upon the surface of the specimen.

10. The system of claim 1, wherein the oblique angle of incidence comprises an angle of incidence from approximately 60° to approximately 80°.

11. The system of claim 1, wherein the collection system comprises a spatial filter configured to reduce unwanted diffraction orders in the first beam of light scattered from the surface of the specimen during use and to reduce unwanted diffraction orders in the second beam of light scattered from the surface of the specimen during use.

12. The system of claim 1, wherein the collection system comprises at least two collectors, and wherein at least the two collectors comprise single dark field collectors, double dark field collectors, near normal dark field collectors, bright field collectors, or any combination thereof.

13. The system of claim 1, wherein defects that can be detected from the collected portions of the first and second beams of light comprise defects above the surface, defects below the surface, defects with varying orientations, or any combination thereof.

14. A method for inspecting a specimen, comprising:
   illuminating a surface of the specimen with a first beam of light at an oblique angle of incidence and with a second beam of light at a substantially normal angle, wherein an intensity of the second beam of light is substantially less than an intensity of the first beam of light, and wherein illuminating the surface comprises:
      generating a beam of light;
      directing the generated beam of light at various angles; and
      splitting the directed beam of light into the first beam of light and the second beam of light;
   collecting at least a portion of the first and second beams of light returned from the surface of the specimen; and
   processing the collected portions of the first and second beams of light such that a presence of defects on the specimen can be detected from the collected portions of the first and second beams of light.

15. The method of claim 14, wherein said illuminating further comprises illuminating the surface of the specimen with the first beam of light and the second beam of light substantially simultaneously.

16. The method of claim 14, wherein said illuminating further comprises illuminating the surface of the specimen with the first beam of light and the second beam of light sequentially.

17. The method of claim 14, wherein said illuminating further comprises reducing a diameter of the second beam of light in one direction such that a shape of the second beam of light incident on the surface of the specimen is substantially the same as a shape of the first beam of light incident on the surface of the specimen.

18. The method of claim 14, wherein said illuminating further comprises increasing a telecentricity of the second beam of light with a focusing lens in a non-telecentric geometry positioned in a path of the second beam of light.

19. The method of claim 14, wherein said illuminating further comprises illuminating the surface of the specimen with an illumination system arranged in a Mach-Zehnder type arrangement.

20. The method of claim 14, wherein a polarization of the first beam of light is substantially orthogonal to a polarization of the second beam of light.

21. The method of claim 14, wherein substantially an entire area of the first beam of light incident upon the surface of the specimen overlaps substantially an entire area of the second beam of light incident upon the surface of the specimen.

22. The method of claim 14, wherein the oblique angle of incidence comprises an angle of incidence from approximately 5° to approximately 80°.

23. The method of claim 14, further comprising reducing unwanted diffraction orders in the first beam of light scattered from the surface of the specimen and in the second beam of light scattered from the surface of the specimen.

24. The method of claim 14, wherein said collecting comprises collecting the first beam of light with at least one collector, and wherein at least the one collector comprises a single dark field collector, a double dark field collector, a near normal dark field collector, or any combination thereof.

25. The method of claim 14, wherein said collecting comprises collecting the second beam of light with at least one collector, and wherein at least the one collector comprises a single dark field collector, a near normal dark field collector, a bright field collector, or any combination thereof.

26. The method of claim 14, wherein the defects that can be detected from the collected portions of the first and second beams of light comprise defects above the surface, defects below the surface, defects with varying orientations, or any combination thereof.

* * * * *